United States Patent [19]

Von Unge

[11] Patent Number: 5,693,818
[45] Date of Patent: Dec. 2, 1997

[54] PROCESS FOR PREPARING PURE SALTS OF PYRIDINYLMETHYL-SULFINYL-1H-BENZIMIDAZOLE

[75] Inventor: Sverker Von Unge, Fjärås, Sweden

[73] Assignee: Astra Aktiebolag, Sodertalje, Sweden

[21] Appl. No.: 256,174

[22] PCT Filed: May 27, 1994

[86] PCT No.: PCT/SE94/00509

§ 371 Date: Jun. 28, 1994

§ 102(e) Date: Jun. 28, 1994

[87] PCT Pub. No.: WO94/27988

PCT Pub. Date: Dec. 12, 1994

[30] Foreign Application Priority Data

May 28, 1993 [SE] Sweden ................................ 9301830

[51] Int. Cl.$^6$ .................................................. C07D 401/12
[52] U.S. Cl. ................................... 546/273.7; 514/338
[58] Field of Search ............................................. 546/273.7

[56] References Cited

FOREIGN PATENT DOCUMENTS

| 0005129 | 4/1981 | European Pat. Off. . |
| 0124495 | 1/1987 | European Pat. Off. . |
| 4035455 | 11/1990 | Germany . |
| 4035455 | 5/1992 | Germany . |

OTHER PUBLICATIONS

Cairns, et al. "Enantioselective HPLC determination . . ." Journal of Chromatography 8,666 (1995) 323–328.

Yamada et al. "Synthesis and isomerization of optical active . . ." Chem. Pharm. Bull. 42(8) (1994) 1679–1681.

K. Miwa et al. Jpn. Pharmacol. Ther. "Proton pump inhibitor in rats, mice and dogs" 18 (1990) 165–187 (transl.).

H. Katsuki et al. "Determination of R(+)– and S(–)–Lansoprazole" Pharmaceutical Research 13(4) (1996) 611–615.

M. Tanaka et al. "Direct determination of pantoprazole enantiomers . . ." Anal. Chem. 68 (1996) 1513–1516.

Erlandsson et al., J. Chromatography vol. 532, pp.305–319 (1990).

*Primary Examiner*—Jane Fan
*Attorney, Agent, or Firm*—White & Case

[57] ABSTRACT

The novel optically pure compounds $Na^+$, $Mg^{2+}$, $Li^+$, $K^+$, $Ca^{2+}$ and $N^+(R)_4$ salts of (+)-5-methoxy-2-[[(4-methoxy-3,5-dimethyl-2-pyridinyl)methyl]sulfinyl]-1H-benzimidazole or (−)-5-methoxy-2-[[(4-methoxy-3,5-dimethyl-2-pyridinyl)methyl]sulfinyl]-1H-benzimidazole, where R is an alkyl with 1–4 carbon atoms, processes for the preparation thereof and pharmaceutical preparations containing the compounds as active ingredients, as well as the use of the compounds in pharmaceutical preparations and intermediates obtained by preparing the compounds.

6 Claims, No Drawings

PROCESS FOR PREPARING PURE SALTS OF PYRIDINYLMETHYL-SULFINYL-1H-BENZIMIDAZOLE

FIELD OF THE INVENTION

The present invention is directed to new compounds with high optical purity, their use in medicine, a process for their preparation and their use in the manufacture of pharmaceutical preparation. The invention also relates to novel intermediates in the preparation of the compounds of the invention.

BACKGROUND OF THE INVENTION

The compound 5-methoxy-2-[[(4-methoxy-3,5-dimethyl-2-pyridinyl)methyl]sulfinyl]-1H-benzimidazole, having the generic name omeprazole, and therapeutically acceptable alkaline salts thereof are described in EP 5129 and EP 124 495, respectively. Omeprazole and its alkaline salts are effective gastric acid secretion inhibitors, and are useful as antiulcer agents. The compounds, being sulfoxides, have an asymmetric center in the sulfur atom, i.e. exist as two optical isomers (enantiomers). It is desirable to obtain compounds with improved pharmacokinetic and metabolic properties which will give an improved therapeutic profile such as a lower degree of interindividual variation. The present invention provides such compounds, which are novel salts of single enantiomers of omeprazole.

The separation of the enantiomers of omeprazole in analytical scale is described in e.g. J. Chromatography, 532 (1990), 305–19 and in a preparative scale in DE 4035455. The latter has been done by using a diastereomeric ether which is separated and thereafter hydrolysed in an acidic solution. Under the acidic conditions needed for hydrolysis of the attached group, omeprazole is quite sensitive and the acid has to be quickly neutralized with a base to avoid degradation of the acid-sensitive compound. In the above mentioned application this is done by adding the reaction mixture containing concentrated sulfuric acid to a concentrated solution of NaOH. This is disadvantageous because there is a great risk of locally reaching pH values between 1–6, which would be devastating for the substance. Moreover, instantaneous neutralisation will create heat which will be difficult to handle in large scale production.

SUMMARY OF THE INVENTION

The present invention in a further aspect provides a novel method for preparing the novel compounds of the invention in large scale. This novel method can also be used in large scale to obtain single enantiomers of omeprazole in neutral form.

There is no example known in the prior art of any isolated or characterized salt of optically pure omeprazole, i.e. single enantiomers of omeprazole neither of any isolated or characterized salt of any optically pure omeprazole analogue.

DETAILED DESCRIPTION OF THE INVENTION

The present invention refers to the new $Na^+$, $Mg^{2+}$, $Li^+$, $K^+$, $Ca^{2+}$ and $N^+(R)_4$ salts of the single enantiomers of omeprazole, where R is an alkyl with 1–4 carbon atoms, i.e. $Na^+$, $Mg^{2+}$, $Li^+$, $K^+$, $Ca^{2+}$ and $N^+(R)_4$ salts of (+)-5-methoxy-2-[[(4-methoxy-3,5-dimethyl-2-pyridinyl)methyl]sulfinyl]-1H-benzimidazole and (−)-5-methoxy-2-[[(4-methoxy-3,5-dimethyl-2-pyridinyl)methyl]sulfinyl]-1H-benzimidazole, where R is an alkyl with 1–4 carbon atoms.

Particularly preferred salts according to the invention are the $Na^+$, $Ca^{2+}$ and $Mg^{2+}$ salts, i.e (+)-5-methoxy-2-[[(4-methoxy-3,5-dimethyl-2-pyridinyl)methyl]sulfinyl]-1H-benzimidazole sodium salt, (−)-5-methoxy-2-[[(4-methoxy-3,5-dimethyl-2-pyridinyl)methyl]sulfinyl]-1H-benzimidazole sodium salt, (+)-5-methoxy-2-[[(4-methoxy-3,5-dimethyl-2-pyridinyl)methyl]sulfinyl]-1H-benzimidazole magnesium salt, (−)-5-methoxy-2-[[(4-methoxy-3,5-dimethyl-2-pyridinyl)methyl]sulfinyl]-1H-benzimidazole magnesium salt, (+)-5-methoxy-2-[[(4-methoxy-3,5-dimethyl-2 -pyridinyl)methyl]sulfinyl]-1H-benzimidazole calcium salt and (−)-5-methoxy-2-[[(4-methoxy-3,5-dimethyl-2-pyridinyl)methyl]sulfinyl]-1H-benzimidazole calcium salt.

Most preferred salts according to the invention are the optically pure $Na^+$ salts of omeprazole according to compounds Ia and Ib

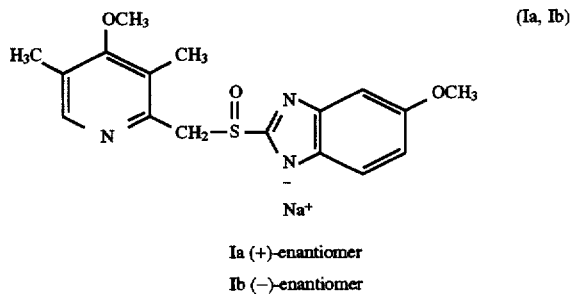

Ia (+)-enantiomer
Ib (−)-enantiomer and the optically pure magnesium salts of omeprazole according to compounds IIa and IIb

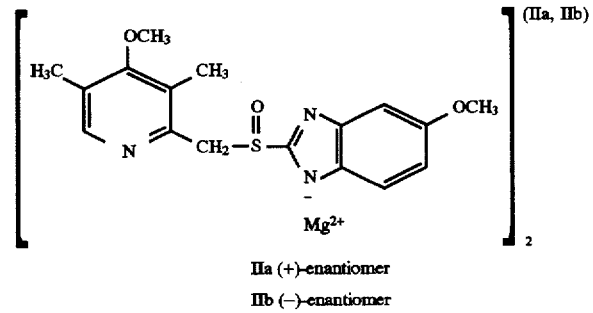

IIa (+)-enantiomer
IIb (−)-enantiomer

With the expression "optically pure $Na^+$ salts of omeprazole" is meant the (+)-enantiomer of omeprazole Na-salt essentially free of the (−)-enantiomer of omeprazole Na-salt and the (−)-enantiomer essentially free of the (+)-enantiomer, respectively. Single enantiomers of omeprazole have hitherto only been obtained as syrups and not as crystalline products. By means of the novel specific method according to one aspect of the invention of preparing the single enantiomers of omeprazole, the salts defined by the present invention are easy to obtain. In addition, the salts, however not the neutral forms, are obtained as crystalline products. Because it is possible to purify optically impure salts of the enantiomers of omeprazole by crystallisation, they can be obtained in very high optical purity, namely ≧99.8% enantiomeric excess (e.e.) even from an optically contaminated preparation. Moreover, the optically pure salts are stable towards racemization both in neutral pH and basic pH, which was surprising since the known deprotonation at the carbon atom between the pyridine ring and the chiral sulphur atom was expected to cause racemization under alkaline conditions. This high stability towards racemization makes it possible to use a single enantiomeric salt of the invention in therapy.

The specific method of preparation of the single enantiomers of omeprazole is a further aspect of the invention as mentioned above and it can be used to obtain the single enantiomers of omeprazole in neutral from as well as the salts thereof.

The compounds according to the invention may be used for inhibiting gastric acid secretion in mammals and man. In a more general sense, the compounds of the invention may be used for the treatment of gastric acid-related diseases and gastrointestinal inflammatory diseases in mammals and man, such as gastric ulcer, duodenal ulcer, reflux esophagitis, and gastritis. Furthermore, the compounds may be used for treatment of other gastrointestinal disorders where gastric antisecretory effect is desirable e.g. in patients on NSAID therapy, in patients with gastrinomas, and in patients with accute upper gastrointestinal bleeding. They may also be used in patients in intensive care situations, and pre- and postoperatively to prevent acid aspiration and stress ulceration. The compound of the invention may also be used for treatment or prophylaxis of inflammatory conditions in mammals, including man, especially those involving lysozymal enzymes. Conditions that may be specifically mentioned are rheumatoid arthritis and gout. The compound of the invention may also be useful in the treatment of psoriasis as well as in the treatment of Helicobacter infections.

Yet a further aspect of the invention is the compound III, which is an intermediate used in the specific method of preparation.

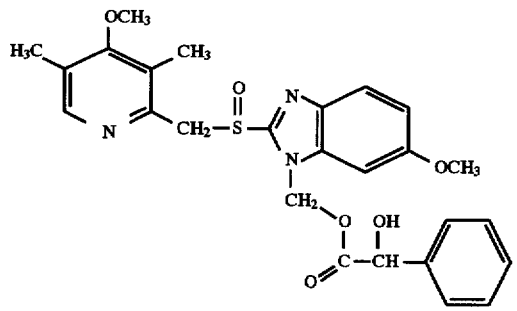

(III)

Preparation

The optically pure compounds of the invention, i.e. the single enantiomers, are prepared by separating the two stereoisomers of a diastereomeric mixture of the following type, 5- or 6-methoxy-2-[[(4-methoxy-3,5-dimethyl-2-pyridinyl)methyl]sulfinyl]-1-[acyloxymethyl]-1H-benzimidazole, formula IV

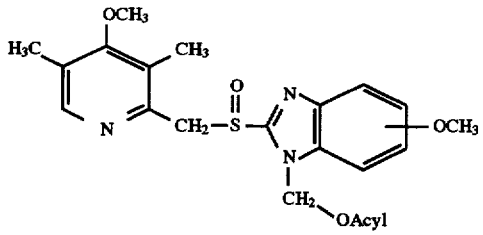

(IV)

wherein the methoxy substituent in the benzimidazole moiety is in position 5 or 6, and wherein the Acyl radical is as defined below, followed by a solvolysis of each separated diastereomer in an alkaline solution. The formed single enantiomers of omeprazole are then isolated by neutralizing aqueous solutions of the salts of the single enantiomers of omeprazole with a neutralizing agent which can be an acid or an ester such as methyl formate.

The Acyl moiety in the diastereomeric ester may be a chiral acyl group such as mandeloyl, and the asymmetric center in the chiral acyl group can have either R or S configuration.

The diastereomeric esters can be separated either by chromatography or fractional crystallization.

The solvolysis usually takes place together with a base in a protic solvent such as alcohols or water, but the acyl group may also be hydrolysed off by a base in an aprotic solvent such as dimethylsulfoxide or dimethylformamide. The reacting base may be $OH^-$ or $R^1O^-$ where $R^1$ can be any alkyl or aryl group.

To obtain the optically pure $Na^+$ salts of the invention, i.e. the single enantiomers of omeprazole $Na^+$ salts, the resulting compound is treated with a base, such as NaOH, in an aqueous or nonaqueous medium, or with $NaOR^2$ wherein $R^2$ is an alkyl group containing 1–4 carbon atoms, or with $NaNH_2$. Also alkaline salts wherein the cation is $Li^+$ or $K^+$ may be prepared using lithium or potassium salts of the above mentioned bases. In order to obtain the crystalline form of the $Na^+$ salt, addition of NaOH in a non-aqueous medium such as a mixture of 2-butanone and toluene, is preferred.

To obtain the optically pure $Mg^{2+}$ salts of the invention, optically pure $Na^+$ salts are treated with an aqueous solution of an inorganic magnesium salt such as $MgCl_2$, whereupon the $Mg^{2+}$ salts are precipitated. The optically pure $Mg^{2+}$ salts may also be prepared by treating single enantiomers of omeprazole with a base, such as $Mg(OR^3)_2$, wherein $R^3$ is an alkyl group containing 1–4 carbon atoms, in a non-aqueous solvent such as alcohol (only for alcoholates), e.g. ROH, or in an ether such as tetrahydrofuran. In an analogous way, also alkaline salts wherein the cation is $Ca^{2+}$ can be prepared, using an aqueous solution of an inorganic calcium salt such as $CaCl_2$.

Alkaline salts of the single enantiomers of the invention are, as mentioned above, beside the sodium salts (compounds Ia and Ib) and the magnesium salts (compound IIa and IIb), exemplified by their salts with $Li^+$, $K^+$, $Ca^{2+}$ and $N^+(R)_4$, where R is an alkyl with 1–4 C-atoms.

For clinical use the single enantiomers, i.e. the optically pure compounds, of the invention are formulated into pharmaceutical formulations for oral, rectal, parenteral or other modes of administrations. The pharmaceutical formulations contain the single enantiomers of the invention normally in combination with a pharmaceutically acceptable carrier. The carrier may be in form of a solid, semi-solid or liquid diluent, or capsule. These pharmaceutical preparations are a further object of the invention. Usually the amount of active compound is between 0.1–95% by weight of the preparation, between 0.2–20% by weight in preparations for parenteral use and between 1–50% by weight in preparations for oral administration.

In the preparation of pharmaceutical formulations in form of dosage units for oral administration the optically pure compound may be mixed with a solid, powdered carrier, such as lactose, saccharose, sorbitol, mannitol, starch, amylopectin, cellulose derivates, gelatin or another suitable carrier, stabilizing substances such as alkaline compounds e.g. carbonates, hydroxides and oxides of sodium, potassium, calcium, magnesium and the like as well as with lubricating agents such as magnesium stearate, calcium stearate, sodium stearyl fumarate and polyethylenglycol waxes. The mixture is then processed into granules or pressed into tablets. Granules and tablets may be coated with an enteric coating which protects the active compound from acid catalysed degradation as long as the dosage form remains in the stomach. The enteric coating is chosen among pharmaceutically acceptable enteric-coating materials e.g. beeswax, shellac or anionic film-forming polymers and the like, if preferred in combination with a suitable plasticizer. To the coating various dyes may be added in order to distinguish among tablets or granules with different amounts of the active compound present.

Soft gelatine capsules may be prepared with capsules containing a mixture of the active compound, vegetable oil, fat, or other suitable vehicle for soft gelatine capsules. Soft gelatine capsules may also be enteric-coated as described above.

Hard gelatine capsules may contain granules or enteric-coated granules of the active compound. Hard gelatine capsules may also contain the active compound in combination with a solid powdered carrier such as lactose, saccharose, sorbitol, mannitol, potato starch, amylopectin, cellulose derivates or gelatin. The capsules may be enteric-coated as described above.

Dosage units for rectal administration may be prepared in the form of suppositories which contain the active substance mixed with a neutral fat base, or they may be prepared in the form of a gelatine rectal capsule which contains the active substance in a mixture with a vegetable oil, paraffin oil or other suitable vehicle for gelatine rectal capsules, or they may be prepared in the form of a ready-made micro enema, or they may be prepared in the form of a dry micro enema formulation to be reconstituted in a suitable solvent just prior to administration.

Liquid preparation for oral administration may be prepared in the form of syrups or suspensions, e.g. solutions or suspensions containing from 0.2% to 20% by weight of the active ingredient and the remainder consisting of sugar or sugar alcohols and a mixture of ethanol, water, glycerol, propylene glycol and/or polyethylene glycol. If desired, such liquid preparations may contain colouring agents, flavouring agents, saccharine and carboxymethyl cellulose or other thickening agents. Liquid preparations for oral administration may also be prepared in the form of dry powder to be reconstituted with a suitable solvent prior to use.

Solutions for parenteral administrations may be prepared as solutions of the optically pure compounds of the invention in pharmaceutically acceptable solvents, preferably in a concentration from 0.1 to 10% by weight. These solutions may also contain stabilizing agents and/or buffering agents and may be manufactured in different unit dose ampoules or vials. Solutions for parenteral administration may also be prepared as dry preparations to be reconstituted with a suitable solvent extemporaneously before use.

The typical daily dose of the active compound will depend on various factors such as for example the individual requirement of each patient, the route of administration and the disease. In general, oral and parenteral dosages will be in the range of 5 to 500 mg per day of active substance.

The invention is illustrated by the following examples.

EXAMPLE 1

Preparation of (+)-5-Methoxy-2-[[(4-methoxy-3,5-dimethyl-2-pyridinyl)methyl]sulfinyl]-1H-benzimidazole Sodium Salt 100 mg (0.3 mmol) of (−)-5-methoxy-2-[[(4-methoxy-3,5-dimethyl-2-pyridinyl)methyl]sulfinyl]-1H--benzimidazole (contaminated with 3% of the (+)-isomer) was dissolved in 1 ml of 2-butanone with stirring. 60 µl of an aqueous solution of 5.0M sodium hydroxide and 2 ml of toluene were added. The resultant mixture was non-homogeneous. In order to obtain a clear solution, more 2-butanone was added (ca 1 ml) and the mixture was stirred at ambient temperature over night. The formed precipitate was filtered off and washed with ether. There was obtained 51 mg (46%) of the title compound as white crystals m.p. (decomposition) 246°–248° C. The optical purity (e.e.) which was analyzed by chiral column chromatography was ≧99.8%. $[\alpha]_D^{20}$=+42.8° (c=0.5%, water).

NMR data are given below.

EXAMPLE 2

Preparation of (−)-5-Methoxy-2-[[(4-methoxy-3,5-dimethyl-2-pyridinyl)methyl]sulfinyl]-1H-benzimidazole Sodium Salt 100 mg (0.3 mmol) of (+)-5-methoxy-2-[[(4-methoxy-3,5-dimethyl-2-pyridinyl)methyl]sulfinyl]-1H--benzimidazole (contaminated with 3% of the-(−)-isomer) was dissolved in 1 ml of 2-butanone with stirring. 60 µl of an aqueous solution of 5.0M sodium hydroxide and 2 ml of toluene were added. The resultant mixture was non-homogeneous. In order to obtain a clear solution, more 2-butanone was added (ca 1 ml) and the mixture was stirred at ambient temperature over night. The formed precipitate was filtered off and washed with ether. There was obtained 56 mg (51%) of the title compound as white crystals m.p. (decomposition) 247°–249° C. The optical purity (e.e.) which was analyzed by chiral column chromatography was ≧99.8%. $[\alpha]_D^{20}$=−44.1° (c=0.5%, water).

NMR data are given below.

EXAMPLE 3

Preparation of (+)-5-Methoxy-2-[[(4-methoxy-3,5-dimethyl-2-pyridinyl)methyl]sulfinyl]-1H--benzimidazole Magnesium Salt 2.9 ml of a 0.1M solution of NaOH was added to 0.10 g (0.29 mmol) (+)-5-methoxy-2-[[(4-methoxy-3,5-dimethyl-2-pyridinyl)methyl]sulfinyl]-1H-benzimidazole. To this mixture 2 ml methylene chloride was added, and after mixing in a separatory funnel the aqueous solution was separated off. A solution of 14 mg (0.145 mmol) MgCl₂ in water was added dropwise. The formed precipitate was isolated by centrifugation, and 52 mg (50%) of the product was isolated as an amorphous powder. The optical purity (e.e.) was 98%, and thus the same as the starting material. The optical purity was determined by chromatography on an analytical chiral column. $[\alpha]_D^{20}$=+101.2° (c=1%, methanol). The Mg content of the sample was found to be 3.0%, shown by atomic absorption spectroscopy.

EXAMPLE 4

Preparation of (+)-5-Methoxy-2-[[(4-methoxy-3,5-dimethyl-2-pyridinyl)methyl]sulfinyl]-1H--benzimidazole Magnesium Salt (−)-5-methoxy-2-[[(4-methoxy-3,5-dimethyl-2-pyridinyl)methyl]sulfinyl]-1H-benzimidazole sodium salt (0.500 g, 1.36 mmol) was dissolved in water (10 ml). To this mixture 10 ml of an aqueous solution of MgCl₂×H₂O (138 mg, 0.68 mmol) was added dropwise and the formed precipitate was isolated by centrifugation. There was obtained 418 mg (86%) of the product as a white powder. The optical purity (ee) of the product was 99.8% which was the same as the optical purity of the starting material. The optical purity was determined by chromatography on an analytical chiral column. $[\alpha]_D^{20}$=+129.9° (c=1%, methanol).

EXAMPLE 5

Preparation of (−)-5-Methoxy-2-[[(4-methoxy-3,5-dimethyl-2-pyridinyl)methyl]sulfinyl]-1H-benzimidazole Magnesium Salt (+)-5-methoxy-2-[[(4-methoxy-3,5-dimethyl-2-pyridinyl)methyl]-sulfinyl]-1H-benzimidazole sodium salt (0.165 g, 0.45 mmol) was dissolved in water (3 ml). To this mixture 2 ml of an aqueous solution of $MgCl_2 \times H_2O$ (46 mg, 0.23 mmol) was added dropwise and the formed precipitate was isolated by centrifugation. There was obtained 85 mg (51%) of the product as a white powder. The optical purity (ee) of the product was 99.9% which was the same or better as the optical purity of the starting material. The optical purity was determined by chromatography on an analytical chiral column. $[\alpha]_D^{20} = -128.2°$ (c=1%, methanol).

TABLE 1

| Ex. | Solvent | NMR data δ ppm |
|---|---|---|
| 1. | DMSO-d$_6$ 500 MHz | 2.20(s, 3H), 2.22(s, 3H), 3.69(s, 3H), 3.72(s, 3H), 4.37(d, 1H), 4.75(d, 1H), 6.54(dd, 1H), 6.96(d, 1H) 7.30(d, 1H), 8.21(s, 1H). |
| 2. | DMSO-d$_6$ 500 MHz | 2.20(s, 3H), 2.22(s, 3H), 3.69(s, 3H), 3.72(s, 3H), 4.38(d, 1H), 4.73(d, 1H), 6.54(dd, 1H), 6.96(d, 1H), 7.31(d, 1H), 8.21(s, 1H). |

Preparation of the synthetic intermediates according to the invention will be described in the following examples.

EXAMPLE 6

Preparation of 6-Methoxy-2-[[(4-methoxy-3,5-dimethyl-2-pyridinyl)methyl]-(R/S)-sulfinyl]-1-[(R)-mandeloyloxymethyl]-1H-benzimidazole A solution of 3.4 g sodium hydroxide in 40 ml water was added to a mixture of 14.4 g (42 mmol) tetrabutylammonium hydrogen sulphate and 6.4 g (42 mmol) (R)-(−)-mandelic acid. The mixture was extracted with 400 ml chloroform. After separation, the organic extract was heated to reflux with 16.6 g (42 mmol) of the racemate of 6-methoxy-2-[[(4-methoxy-3,5-dimethyl-2-pyridinyl)methyl]-sulfinyl]-1-[chloromethyl]-1H--benzimidazole. Evaporation of the solvent was followed by dilution with 100 ml dichloromethane and 700 ml ethyl acetate. The mixture was washed with 3×200 ml water and the organic solution was dried over MgSO$_4$ and then evaporated. The crude material was purified by recrystallization from 100 ml acetonitrile, giving 8.1 g of the title compound (38%) as a diastereomeric mixture.

NMR data are given below.

EXAMPLE 7

Separation of the More Hydrophilic Diastereomer of 6-Methoxy-2-[[(4-methoxy-3,5-dimethyl-2-pyridinyl)methyl]-(R/S)-sulfinyl]-1-[(R)-mandeloyloxymethyl]1H-benzimidazole The diastereomers of the title compound in Example 6 were separated using reversed phase chromatography (HPLC). Approximately 300 mg of the diastereomeric mixture was dissolved in 10 ml hot acetonitrile which was diluted with 10 ml of a mixture of aqueous 0.1M ammoniumacetate and acetonitrile (70/30). The solution was injected to the column and the compounds were eluted with a mixture of aqueous 0.1M ammoniumacetate and acetonitrile (70/30). The more hydrophilic isomer was easier to obtain pure than the less hydrophilic one. The work up procedure for the fraction which contained pure isomer was as follows; extraction with dichloromethane, washing the organic solution with aqueous 5% sodium hydrogen carbonate solution, drying over Na$_2$SO$_4$ and evaporation of the solvent on a rotavapor (at the end of the evaporation the removal of acetonitrile was facilitated by adding more dichloromethane). Using 1.2 g of the diastereomeric mixture with the above mentioned technique, the more hydrophilic isomer, 410 mg, was obtained in a pure state as a colourless syrup.

NMR data are given below.

EXAMPLE 8

Preparation of 6-Methoxy-2-[[(4-methoxy-3,5-dimethyl-2-pyridinyl)methyl]-(R/S)-sulfinyl]-1-[(S)-mandeloyloxymethyl]-1H-benzimidazole The product was obtained from 8.1 g (202 mmol) sodium hydroxide in 100 ml water, 34.4 g (101 mmol) tetrabutylammonium hydrogen sulfate, 15.4 g (101 mmol) (S)-(+)-mandelic acid and 39.9 g (101 mmol) of the racemate of 6-methoxy-2-[[(4-methoxy-3,5-dimethyl-2-pyridinyl) methyl]-sulfinyl]-1-[chloromethyl]-1H-benzimidazole using the same procedure as in Example 6. Recrystallization from 100 ml acetonitrile yielded 21.3 g, i.e. 41% of the title compound as a diastereomeric mixture.

NMR data are given below.

EXAMPLE 9

Separation of the More Hydrophilic Diastereomer of 6-Methoxy-2-[[(4-methoxy-3,5-dimethyl-2-pyridinyl)methyl]-(R/S)-sulfinyl]-1-[(S)-mandeloyloxymethyl]-1H-benzimidazole The diastereomers of the title compound in Example 8 were separated using reversed phase chromatography (HPLC) in the same way as in Example 7, but using the diasteromeric mixture of 6-methoxy-2-[[(4-methoxy-3,5-dimethyl-2-pyridinyl)methyl]-(R/S)-sulfinyl]-1-[(S)-mandeloloxymethyl]-1H-benzimidazole instead of the (R)-mandelic ester used in Example 7. Using 2.1 g of the diastereomeric mixture, the more hydrophilic isomer, 760 mg, was obtained in a pure state as a colourless syrup.

NMR data are given below.

EXAMPLE 10

Preparation of (−)-5-Methoxy-2-[[(4-methoxy-3,5-dimethyl-2-pyridinyl)methyl]-sulfinyl]-1H-benzimidazole 0.23 g (0.45 mmol) of the more hydrophilic diastereomer of 6-methoxy-2-[[(4-methoxy-3,5-dimethyl-2-pyridinyl) methyl]sulfinyl]-1-[(R)-mandeloyloxymethyl]-1H-benzimidazole was dissolved in 15 ml methanol. A solution of 36 mg (0.9 mmol) sodium hydroxid in 0.45 ml water was added, and after 10 minutes the mixture was evaporated on a rotavapor. The residue was partitioned between 15 ml water and 15 ml dichloromethane. The organic solution was extracted with 15 ml water and to the combined aqueous solutions was added 85 μl (1.4 mmol) methyl formate. After 15 minutes the mixture was extracted with 3×10 ml dichloromethane. The organic solution was dried over Na$_2$SO$_4$ and then evaporated. There was obtained 0.12 g (77%) of the title compound as a colourless syrup. The optical purity (e.e.) which was analyzed by chiral column chromatography was 94%. $[\alpha]_D^{20} = -155°$ (c=0.5%, chloroform).

NMR data are given below.

EXAMPLE 11

Preparation of (+)-5-Methoxy-2-[[(4-methoxy-3,5-dimethyl-2-pyridinyl)methyl]-sulfinyl]-1H-benzimidazole 0.76 g (1.5 mmol) of the more hydrophilic diastereomer of 6-methoxy-2-[[(4-methoxy-3,5-dimethyl-2-pyridinyl)

methyl]sulfinyl]-1-[(S)-mandeloyloxymethyl]-1H-benzimidazole was dissolved in 50 ml methanol. A solution of 0.12 mg (3.0 mmol) sodium hydroxid in 1.5 ml water was added, and after 10 minutes the mixture was evaporated on a rotavapor. The residue was partitioned between 25 ml water and 25 ml dichloromethane. The organic solution was extracted with 25 ml water and to the combined aqueous solutions was added 200 µl (3.2 mmol) methyl formate. After 15 minutes the mixture was extracted with 3×25 ml dichloromethane. The organic solution was dried over $Na_2SO_4$ and then evaporated. There was obtained 0.42 g (81%) of the title compound as a colourless syrup. The optical purity (e.e.) which was analyzed by chiral column chromatography was 98%. $[\alpha]_D^{20}=+157°$ (c=0.5%, chloroform).

NMR data are given below.

TABLE 2

| Ex. | Solvent | NMR data δ ppm |
|---|---|---|
| 6. | CDCl₃ 500 MHz | 2.18(s, 3H), 2.20(s, 3H), 2.36(s, 3H), 2.39(s, 3H), 3.77(s, 3H), 3.78(s, 3H), 3.82(s, 3H), 3.87(s, 3H), 4.80(d, 1H), 4.88(d, 1H), 5.0(m, 2H), 5.34(s, 2H), 6.43(d, 1H), 6.54(d, 1H), 6.6–6.7(m, 2H), 6.90 (d, 1H), 6.95–6.98(m, 2H), 7.01(d, 1H), 7.2–7.3 (m, 6H), 7.37(m, 2H), 7.44(m, 2H), 7.58(d, 1H), 7.62 (d, 1H), 7.95(s, 1H), 7.97(s, 1H). |
| 7. | CDCl₃ 500 MHz | 2.20(s, 3H), 2.36(s, 3H), 3.78(s, 3H), 3.82(s, 3H), 4.80(d, 1H), 5.00(d, 1H), 5.35(d, 1H), 6.43(d, 1H), 6.63(d, 1H), 6.90(d, 1H), 6.97(dd, 1H), 7.2–7.3 (m, 3H), 7.37(m, 2H), 7.62(d, 1H), 7.97(s, 1H). |
| 8. | CDCl₃ 500 MHz | 2.19(s, 3H), 2.20(s, 3H), 2.36(s, 3H), 2.39(s, 3H), 3.77(s, 3H), 3.78(s, 3H), 3.83(s, 3H), 3.87(s, 3H), 4.80(d, 1H), 4.88(d, 1H), 5.0(m, 2H), 5.34(s, 2H), 6.43(d, 1H), 6.54(d, 1H), 6.6–6.7(m, 2H), 6.90 (d, 1H), 6.96–6.98(m, 2H), 7.01(d, 1H), 7.2–7.3 (m, 6H), 7.37(m, 2H), 7.44(m, 2H), 7.58(d, 1H), 7.62 (d, 1H), 7.95(s, 1H), 7.97(s, 1H). |
| 9. | CDCl₃ 500 MHz | 2.20(s, 3H), 2.36(s, 3H), 3.78(s, 3H), 3.82(s, 3H), 4.80(d, 1H), 5.00(d, 1H), 5.35(d, 1H), 6.43(d, 1H), 6.63(d, 1H), 6.90(d, 1H), 6.97(dd, 1H), 7.2–7.3 (m, 3H), 7.37(m, 2H), 7.62(d, 1H), 7.97(s, 1H). |
| 10. | CDCl₃ 300 MHz | 2.18, (s, 3H), 2.22(s, 3H), 3.68(s, 3H), 3.83(s, 3H), 4.77(m, 2H), 6.93(dd, 1H), ≈7.0(b, 1H), ≈7.5 (b, 1H), 8.19(s, 1H). |
| 11. | CDCl₃ | 2.21(s, 3H), 2.23(s, 3H), 3.69(s, 3H), 3.84(s, 3H), 4.76(m, 2H), 6.94(dd, 1H), ≈7.0(b, 1H), ≈7.5(b, 1H), 8.20(s, 1H). |

The best mode of carrying out the invention known at present is to use the sodium salts of the optically pure compounds of the invention, thus the compounds described in Example 1 and Example 2.

Pharmaceutical preparations containing the compounds of the invention as active ingredient are illustrated in the following formulations.

Syrup

A syrup containing 1% (weight per volume) of active substance was prepared from the following ingredients:

| | |
|---|---|
| Compound according to Example 2 | 1.0 g |
| Sugar, powder | 30.0 g |
| Saccharine | 0.6 g |
| Glycerol | 5.0 g |
| Flavouring agent | 0.05 g |
| Ethanol 96% | 5.0 g |
| Distilled water q.s. to a final volume of | 100 ml |

Sugar and saccharine were dissolved in 60 g of warm water. After cooling the active compound was added to the sugar solution and glycerol and a solution of flavouring agents dissolved in ethanol were added. The mixture was diluted with water to a final volume of 100 ml.

Enteric-coated Tablets

An enteric coated tablet containing 50 mg of active compound was prepared from the following ingredients:

| | | |
|---|---|---|
| I | Compound according to Example 3 as Mg salt | 500 g |
| | Lactose | 700 g |
| | Methyl cellulose | 6 g |
| | Polyvinylpyrrolidone cross-linked | 50 g |
| | Magnesium stearate | 15 g |
| | Sodium carbonate | 6 g |
| | Distilled water | q.s. |
| II | Cellulose acetate phthalate | 200 g |
| | Cetyl alcohol | 15 g |
| | Isopropanol | 2000 g |
| | Methylene chloride | 2000 g |

I Compound according to Example 3, powder, was mixed with lactose and granulated with a water solution of methyl cellulose and sodium carbonate. The wet mass was forced through a sieve and the granulate dried in an oven. After drying the granulate was mixed with polyvinylpyrrolidone and magnesium stearate. The dry mixture was pressed into tablet cores (10 000 tablets), each tablet containing 50 mg of active substance, in a tabletting machine using 7 mm diameter punches.

II A solution of cellulose acetate phthalate and cetyl alcolhol in isopropanol/methylene chloride was sprayed onto the tablets I in an Accela Cola$^R$, Manesty coating equipment. A final tablet weight of 110 mg was obtained.

Solution for Intravenous Administration

A parenteral formulation for intravenous use, containing 4 mg of active compound per ml, was prepared from the following ingredients:

| | |
|---|---|
| Compound according to Example 2 | 4 g |
| Sterile water to a final volume of | 1000 ml |

The active compound was dissolved in water to a final volume of 1000 ml. The solution was filtered through a 0.22 µm filter and immediately dispensed into 10 ml sterile ampoules. The ampoules were sealed.

Capsules

Capsules containing 30 mg of active compound were prepared from the following ingredients:

| | |
|---|---|
| Compound according to Example 1 | 300 g |
| Lactose | 700 g |
| Microcrystalline cellulose | 40 g |
| Hydroxypropyl cellulose low-substituted | 62 g |
| Disodium hydrogen phosphate | 2 g |
| Purified water | q.s. |

The active compound was mixed with the dry ingredients and granulated with a solution of disodium hydrogen phosphate. The wet mass was forced through an extruder and spheronized and dried in a fluidized bed dryer.

500 g of the pellets above were first coated with a solution of hydroxypropyl methylcellulose, 30 g, in water, 750 g, using a fluidized bed coater. After drying, the pellets were coated with a second coating as given below:

| Coating solution: | |
|---|---|
| Hydroxypropyl methylcellulose phthalate | 70 g |
| Cetyl alcohol | 4 g |
| Acetone | 200 g |
| Ethanol | 600 g |

The final coated pellets were filled into capsules.

Suppositories

Suppositories were prepared from the following ingredients using a welding procedure. Each suppository contained 40 mg of active compound.

| | |
|---|---|
| Compound according to Example 2 | 4 g |
| Witepsol H-15 | 180 g |

The active compound was homogenously mixed with Witepsol H-15 at a temperature of 41° C. The molten mass was volume filled into pre-fabricated suppository packages to a net weight of 1.84 g. After cooling the packages were heat sealed. Each suppository contained 40 mg of active compound.

Stability Towards Racemization at Different pH:es

The stability of the optically pure compounds of the invention towards racemization has been measured at low concentrations in refrigerator in aqueous buffer solutions at pH 8, 9.3, 10 and 11.2. The stereochemical stability was measured by comparing the optical purity for the (−)-isomer of 5-methoxy-2-[[(4-methoxy-3,5-dimethyl-2-pyridinyl)-methyl]sulfinyl]-1H-benzimidazole in buffer solution immediately after dissolving and after several days. The measurement was performed by chromatography on an analytical chiral column. The surprising high stereochemical stability in alkaline conditions for the compounds of invention is exemplified by the fact that no racemization for the test compound was obtained at pH 11.2 even after 21 days. At pH 8, 9.3 and 10, the chemical degradation of the compound is more apparent which makes the racemization measurement more difficult to perform, however at none of these pH values a detectable racemization was obtained after 16 days.

In another racemization experiment with the optically pure compounds of the invention, an aqueous phosphate buffer solution (pH=11) of the (+)-isomer of 5-methoxy-2-[[(4-methoxy-3,5-dimethyl-2-pyridinyl)methyl]sulfinyl]-1H-benzimidazole (c=10⁻⁵M) was warmed for 26 hours at 37° C. without any racemization at all being observed.

I claim:

1. A process for the preparation of (+)-5-methoxy-2-(((4-methoxy-3,5-dimethyl-2-pyridinyl)methyl)sulphinyl)-1H-benzimidazole and (−)-5-methoxy-2-(((4-methoxy-3,5-dimethyl-2-pyridinyl)methyl)sulphinyl)-1H-benzimidazole enantiomers comprising: separating a diastereomeric ester of formula IV

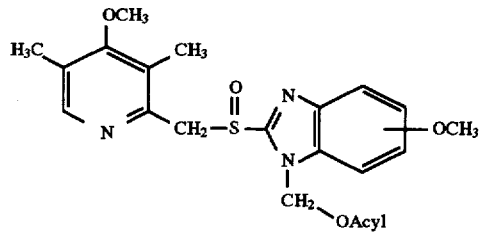

wherein Acyl designates a chiral acyl group, having either R or S configuration; and dissolving each of the separated diastereomers in an alkaline solution of above about pH 7 so as to hydrolyze the acyloxymethyl group off from the separated diastereomers to give the optically pure intact enantiomers which are neutralized with a neutralizing agent which can be an acid or an ester; the pH being maintained at or above about 7 throughout the process.

2. The process according to claim 1 wherein the diastereomers are separated by chromatography or fractional crystallization.

3. The process according to claim 1 wherein the solvolysis is performed in alkaline solution wherein the pH is more than about 7, containing a base in a protic solvent or a base in an aprotic solvent.

4. The process according to claim 1 wherein the chiral acyl group is mandeloyl.

5. The process according to claim 1 or 3 wherein the protic solvent comprises alcohols or water; and wherein the aprotic solvent comprises dimethyl sulfoxide or dimethylformamide.

6. The process according to claim 1 wherein the neutralizing agent is methyl formate.

* * * * *